(12) United States Patent
Dugal et al.

(10) Patent No.: US 7,692,042 B2
(45) Date of Patent: Apr. 6, 2010

(54) PROCESS FOR PREPARING ANILINE

(75) Inventors: Markus Dugal, Kempen (DE); Franz-Ulrich Von Gehlen, Krefeld (DE); Stefan Wershofen, Mönchengladbach (DE); Andre Lago, Shanghai (CN); Peter Lehner, Ratingen (DE); Benie Marotz, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 18 days.

(21) Appl. No.: 11/706,444

(22) Filed: Feb. 15, 2007

(65) Prior Publication Data

US 2007/0203364 A1   Aug. 30, 2007

(30) Foreign Application Priority Data

Feb. 18, 2006   (DE) .................. 10 2006 007 620

(51) Int. Cl.
   *C07C 29/86*   (2006.01)
(52) U.S. Cl. ........................................ 564/437
(58) Field of Classification Search ............... None
   See application file for complete search history.

(56) References Cited

U.S. PATENT DOCUMENTS

| 3,136,818 A | 6/1964 | Sperber et al. ............... 260/580 |
| 3,871,445 A | 3/1975 | Wanka et al. ................ 165/107 |
| 5,808,157 A | 9/1998 | Langer et al. ................ 564/422 |
| 5,877,350 A | 3/1999 | Langer et al. ................ 564/423 |
| 2005/0080294 A1 | 4/2005 | Renner et al. ................ 564/437 |

FOREIGN PATENT DOCUMENTS

| DE | 34 14 714 C2 | 6/1986 |
| JP | 49-35341 | 4/1974 |
| JP | 08-295654 | 11/1996 |

*Primary Examiner*—Paul A Zucker
*Assistant Examiner*—Yevegeny Valenrod
(74) *Attorney, Agent, or Firm*—Lyndanne M. Whalen; Noland J. Cheung

(57) ABSTRACT

Crude aniline is produced by hydrogenating nitrobenzene in the presence of a catalyst. This crude aniline is then purified by means of a single-step or multi-step distillation process in which aqueous alkali metal hydroxide solution is added to the crude aniline prior to distillation and/or during distillation of the crude aniline.

12 Claims, No Drawings

PROCESS FOR PREPARING ANILINE

BACKGROUND OF THE INVENTION

The present invention is directed to a process for preparing aniline including simplified purification of aniline by distillation. In the purification stage of the process, aqueous alkali metal hydroxide solution is added to the crude aniline prior to distillation and/or during distillation of the crude aniline to facilitate separation by distillation of phenolic components from the crude aniline.

Aniline is an important intermediate, e.g., for preparing methylenediphenyl diisocyanate (MDI), and is generally produced on an industrial scale by catalytic hydrogenation of nitrobenzene in the gas or liquid phase (See, e.g., DE-OS 2201528, DE-OS 3414714, U.S. Pat. No. 3,136,818, EP-A-0696573 and EP-A-0696574). In addition to the target product aniline, secondary products such as phenol or aminophenols are also formed during the hydrogenation reaction. These secondary products have to be removed by distillation before further use of aniline in subsequent processes. In particular, the separation of phenol and aniline presents a large challenge to distillation engineering due to their very close boiling points. This difficulty is reflected in the use of distillation columns with high separating power and high reflux ratios, with correspondingly high investment and energy costs.

JP-A-49-035341 describes an alternative process in which the crude aniline is brought into contact with solid alkali materials (e.g. solid sodium hydroxide) in a fixed bed and only then passed into the distillation apparatus, or in which the distillation is performed in the presence of the solid alkali material in concentrations of from 0.1-3 wt. %, with respect to the amount of aniline being distilled. This simplifies the separation of color-critical components such as aminophenols. However, the disadvantages of this process are the use of high molar excesses of the solid alkali materials with respect to the acidic secondary components being removed and the impossibility of accurate dosage of the alkaline compounds, which can lead to corrosion problems, precipitations and highly viscous bottom phases in the distillation column in the case of overdosage and to incomplete removal of the critical components in the case of underdosage.

JP-A-08-295654 describes, as an alternative to removal by distillation of phenolic compounds from aniline, an extraction with dilute aqueous caustic soda (or caustic potash) solution. In this disclosed process, the phenol is transferred to the aqueous phase as sodium phenolate and the sodium phenolate is removed as the upper phase by means of subsequent phase separation. A molar ratio of NaOH:phenol in the range of from 3:1-100:1 is required for effective reduction of the phenol content. The disadvantages of this process are the high NaOH consumption (molar excess), the production of a Na phenolate-containing effluent that leads to additional disposal costs and additional investment costs for the extraction process.

SUMMARY OF THE INVENTION

The present invention provides a process for preparing aniline in which an aqueous alkali metal hydroxide solution is added to the crude aniline before and/or during distillation to purify the crude aniline.

DETAILED DESCRIPTION OF THE INVENTION

In the process of the present invention, crude aniline is produced by hydrogenation of nitrobenzene in the presence of a catalyst. This crude aniline is then purified by single- or multi-stage distillation. A key feature of the process of the present invention is the addition of an aqueous alkali metal hydroxide solution to the crude aniline prior to distillation and/or during distillation of the crude aniline. The amount of added aqueous alkali metal hydroxide solution is adjusted so that the molar ratio of alkali metal hydroxide to the total amount of phenolic compounds present in the crude aniline is between 0.1:1 and 10:1, preferably between 0.5:1 and 1.5:1, most preferably between 0.8:1 and 1.2:1.

In addition to phenol and phenolate, the term phenolic compounds also includes those benzene derivatives that contain other functional groups in addition to the OH function, such as aminophenols.

The process of the present invention is characterised by simplified working up of the crude aniline. The addition of small amounts of aqueous caustic soda, preferably immediately before the crude aniline stream is fed into the distillation apparatus, enables simplified separation of the phenolic components by distillation.

In comparison with the prior art described in JP-A-49-035341, the process of the present invention offers the advantage of accurate stoichiometric or targeted super- or sub-stoichiometric dosage of alkali metal hydroxide, with respect to the phenolic compounds present in the aniline. This control of the amount of alkali metal hydroxide avoids the problems identified with respect to the mode of operation described in JP-A-49-035341. In comparison with the process described in JP-A-08-295654, the process of the present invention offers the advantage of avoiding phenolate-containing effluents, and also the avoidance of additional extraction steps with phase separation.

In the process of the present invention, on combining the alkali metal hydroxide solution with the crude aniline prior to distillation or with a stream that occurs during distillation (for example, a liquid stream that contains aniline), a solution or optionally an emulsion is produced. In this solution or emulsion, phenolic compounds that are present are converted into high-boiling phenolates by reaction with the alkali metal hydroxide. Distillation and separation of the phenolates formed thus take place simultaneously in one step in the process of the present invention. The separating costs and the result of the separation process are thus optimized as compared with the process in the prior art.

The process of the present invention includes the hydrogenation of nitrobenzene. Any of the conventional industrial processes for hydrogenation of nitrobenzene may be used. The hydrogenation of nitrobenzene is preferably performed in the gas phase on fixed heterogeneous supported catalysts (e.g., on Pd on aluminum oxide or on carbon supports), in fixed bed reactors at an absolute pressure of 2-50 bar and a temperature in the range from 250-500° C. under adiabatic conditions using a circulating gas procedure, i.e., with recycling of the unreacted hydrogen from the hydrogenation reaction. Suitable processes are disclosed, for example, in EP-A-0696573 and EP-A-0696574.

Sodium or potassium hydroxide solutions are preferably used as the aqueous alkali metal hydroxide solution(s) in the process of the present invention. In principle, the use of any alkaline earth metal hydroxides or other water-soluble basic compounds such as alkali or alkaline earth metal carbonates or hydrogen carbonates is also possible.

The concentration of alkali metal hydroxide in the aqueous alkali metal hydroxide solution used in the process of the present invention is preferably between 0.1 and 55 wt. %, more preferably between 1 and 50 wt. %, most preferably between 3 and 35 wt. %, based on the weight of aqueous alkali metal solution.

Too high a concentration of alkali metal hydroxide in the aqueous alkali metal hydroxide solution used impairs the dosage accuracy. Too low a concentration of alkali metal hydroxide in the aqueous alkali metal hydroxide solution used increases the water input to the distillation column, which leads to increased energy consumption. The amount of alkali metal hydroxide solution introduced is governed by the concentration of phenolic compounds present in the crude aniline (which can be determined by, e.g., gas chromatographic methods), and by the concentration of the alkali metal hydroxide solution. The amount of aqueous alkali metal hydroxide solution added or introduced is preferably adjusted so that the molar amount of phenolic compounds present in the crude aniline corresponds to the molar amount of alkali metal hydroxide present in the aqueous alkali metal hydroxide solution or so that a slight excess of alkali metal hydroxide is present. However, the stoichiometry of the addition of aqueous alkali metal hydroxide solution can also deliberately be adjusted in the direction of a molar excess or a clear molar deficiency of alkali metal hydroxide as compared with phenolic compounds.

In the process of the present invention, addition of the alkali metal hydroxide solution to the crude aniline takes place before distillation and/or during distillation of the crude aniline. Addition of the alkali metal hydroxide solution to the crude aniline preferably takes place immediately (i.e., normally not more than 15 minutes) before distillation. However, it may also take place during distillation, for example, to a liquid stream that contains aniline in between two distillation steps or into a liquid reflux stream that contains aniline. Addition of the alkali metal hydroxide solution preferably takes place via a metering pump in which the rate of flow can be adjusted manually or via an automatic control system. Mixing of the alkali metal hydroxide solution with the crude aniline flowing into the distillation step or with a stream that contains aniline and that arises during distillation may take place in a variety of ways, e.g., by means of static mixing elements, a stirred tank, pumps or by natural convection.

Alternatively, or in addition to the addition of alkali metal hydroxide solution to the stream flowing into the distillation column, the introduction of alkali metal hydroxide solution may also take place at the base or to the liquid circulating to the base or to the reflux stream of the column.

Working up the mixture of alkali metal hydroxide solution and crude aniline by distillation can take place in a variety of ways by adjusting a wide range of conditions. The distillation may be performed in one or several steps in a variety of types of column, preferably in conventional rectifying columns or in those specified as dividing wall distillation columns and with a variety of inserts, such as perforated plates, valve trays or bubble-cap trays, loose packing or stacked packing. Other embodiments are also possible. Distillation is preferably performed in one distillation column or in two or three distillation columns connected in series. The operating parameters, head pressure and reflux ratio always have to be chosen as a function of the composition of the crude aniline, the specification/purity of the purified aniline required (pure aniline) and the separating stages available. The separation of low-boiling components such as water, benzene, cyclohexane, cyclohexylamine, cyclohexanone and higher boiling components (e.g., phenol, alkali metal phenolate, aminophenols, alkali metal aminophenolates, phenylenediamines, diphenylamine etc.) may take place in different columns or alternatively, in a preferred embodiment, combined in one column with the low-boiling components being withdrawn at the head, the high-boiling components being withdrawn at the base and the pure aniline being withdrawn in a side-stream. Purification of crude aniline by distillation takes place in a side-stream column in a preferred embodiment, more preferably in a dividing wall distillation column, with the low-boiling components being withdrawn at the head, the high-boiling components being withdrawn at the base and pure aniline being withdrawn in a side-stream. Furthermore, the base-product from separation of the high-boiling components may optionally be further concentrated in a residuals column in order to minimize the loss of aniline.

Aniline that has been separated in a residual column is generally recycled into the main distillation stage. The concentrated sump phase of the residual column is normally subjected to incineration.

Optionally the sump phase of the main distillation sage, which is performed after addition of alkali metal hydroxide solution, can be partially discharged and then washed with water or diluted alkali metal hydroxide solution in order to reduce the concentration of phenolate salt in the sump phase of the distillation column. This can be of advantage to achieve a higher residue concentration (lower product loss) in the sump phase during distillation without causing problems by fouling, solid precipitation or strong viscosity increase. This washing step can be performed in various suitable apparatuses such as mixer settler apparatuses, extraction columns or a combination of static mixing elements and phase separators. The water used for the washing step can be taken from any source, however the process water being generated in the nitrobenzol hydrogenation step is preferred in order to minimize waste water streams. The washing step can be carried out in one or multiple steps with temperatures variable over a wide range preferably between 10° C. and 150° C. and with variable phase ratios. After washing and phase separation the organic sump phase can be recycled into any part of the distillation column, preferably directly into the sump phase circulation loop. The phenolate containing aqueous phase from the sump washing step is generally discharged to biological waste water treatment. Optionally residual aniline in the water phase can be removed before the waste water treatment by an additional stripping step. Alternatively the phenolate containing water phase can be incinerated, if necessary after further concentration.

The purified aniline obtained in this way preferably contains less than 0.01 wt. %, most preferably less than 0.005 wt. %, of phenolic compounds in toto, with respect to the weight of aniline.

The aniline and alkali metal hydroxide solution may be fed to the distillation column at any position in the column, but introduction preferably takes place in the middle of the column or in the lower half of the column, depending on the concentration profile for aniline in the distillation column. The column may have a stripping and/or strengthening section. The inflow temperature in the column, as well as the base temperature, head pressure and reflux ratio are adjustable and can be adjusted to the actual separation task as well as to the qualitative, operational and economic requirements. The temperature at the head of the column is set in accordance with the pre-adjustments of the parameters mentioned and the composition of the liquid phase and the vapor phase in the column. Preferred conditions for operating parameters for the distillation column(s) are absolute pressures of 10-1000 mbar, most preferably 10-500 mbar and reflux ratios of 0.1-3, most preferably 0.3-0.8.

In a preferred embodiment of the process of the present invention, the introduction of alkali metal hydroxide solution takes place in the stream of crude aniline flowing into a low-boiling column in which the low-boiling components and water are removed via the head of the column. The mixture being produced at the base that contains aniline and alkali metal hydroxide is then taken to a further distillation step (removal of high-boiling components or pure distillation). Optionally, concentration of the base mixture from separation of the high-boiling components or pure distillation then takes place on a residuals column, wherein the aniline recovered from the head of the residuals column can be recycled to the column for separation of high-boiling components or pure distillation or to the low-boiling components column or to an upstream phase separation step.

In another preferred embodiment, the aniline and alkali metal hydroxide solution are introduced to a combined low-boiling component and high-boiling component column (side-stream column), wherein the low-boiling components are taken away via the head, the high-boiling components are taken from the base and the pure aniline is taken away as a side-stream. This side-stream column can be made up as a conventional column (without separating partitions) or as a dividing wall distillation column. This embodiment, in which a side-stream column or a dividing wall distillation column is used, requires phase separation of the condensed vapors withdrawn at the head containing azeotropic water/aniline and the low-boiling components. Water and low-boiling components dissolved in the aqueous phase are preferably taken away; the aniline is preferably recycled to the column.

The vapors withdrawn at the head of the side-stream column in this embodiment of the process of the present invention are preferably condensed in a two-stage condensation process. The first condenser then preferably partially condenses the higher-boiling components in the vapors. In the second downstream condenser, the low-boiling components that have passed through the first stage are preferably condensed and can thus be removed separately. The partial condensate from the first condenser is taken to a phase separation procedure. Water and the low-boiling components dissolved in the aqueous phase are preferably taken away and the aniline is preferably returned to the column.

Some of the pure aniline withdrawn in the side-stream is preferably fed to the side-stream column as a reflux stream below the withdrawal point of the side-stream. Side-stream withdrawal may be designed as total withdrawal or as partial withdrawal. In both cases, targeted adjustment of the reflux ratio can be achieved.

In another embodiment of the process of the present invention, one or more distillation steps or other processing steps may be provided upstream of the metering of alkali metal hydroxide solution into the crude aniline. For instance, low-boiling components may be removed by distillation before the addition of alkali metal hydroxide solution. After the metering procedure, the high-boiling components are then separated in a downstream pure column with removal of the pure aniline as the head product and optionally, concentration of the base products in another distillation step (residuals column).

The aniline obtained by the process of the present invention may then be reacted with formaldehyde in the presence of an acid catalyst to give di- and polyamines of the diphenylmethane series by any of the processes disclosed in the prior art. The di- and polyamines can then be reacted with phosgene to give the corresponding di- and polyisocyanates in the diphenylmethane series by any of the processes disclosed in the prior art.

EXAMPLES

In the following examples, variants of the process of the present invention are illustrated.

General Preliminary Remarks on Performing the Trials:

The following examples were performed under steady-state operating conditions in a mini-plant laboratory unit.

In each of Examples 1, 2, 3 and 5, combination of and thorough mixing of the crude aniline with the alkali metal hydroxide solution took place before feeding to the distillation column. In Example 4, the alkali metal hydroxide solution was added to the reflux stream of the side-stream of the column. The alkali metal hydroxide solution was metered in different defined concentrations, depending on the phenol concentration in the crude aniline and the actual depletion required, taking into account the amount of water expected to be produced as head product. The amount of water added to distillation in the form of alkali metal hydroxide solution had a direct effect on the energy consumption required and thus on the economic viability of the process. Furthermore, the hydrodynamics also changed as a function of the concentration of water in the feedstock and thus the separating performance of the column inserts used also changed.

The crude aniline used contained the following key components in the concentration ranges (with respect to weight) given below:

| | wt. % |
|---|---|
| benzene | 100-2000 ppm |
| aniline | 99.5-99.9 wt. % |
| phenol | 200-1000 ppm |
| diphenylamine | 40-1500 ppm |

Taking into account the boundary conditions cited above and the phenol depletion desired, the following trials in accordance with the invention were performed by way of example.

Example 1

32 wt. % NaOH solution was metered into the crude aniline in the molar ratio of phenol to NaOH of 1:1.3. The two liquids were mixed in a static mixer. The column was operated at an absolute pressure of 133 mbar and a reflux ratio R/E=0.9 under steady-state operating conditions.

The crude aniline used contained the key components in the following concentrations:

| | wt. % |
|---|---|
| benzene | 0.0225% |
| aniline | 99.9314% |
| phenol | 0.0252% |
| diphenylamine | 0.0040% |

After direct addition of the NaOH solution to the crude aniline and mixing in a static mixer and subsequent distillation, the product with the following concentrations was withdrawn in the side-stream:

|            | wt. %    |
|------------|----------|
| benzene      | 0.0002%  |
| aniline      | 99.9975% |
| phenol       | 0.0009%  |
| diphenylamine | 0.0000%  |

Example 2

32 wt. % NaOH solution was metered into crude aniline in the molar ratio of phenol to NaOH of 1:1.4. The two liquids were mixed using a gear pump. The column was operated at an absolute pressure of 133 mbar and a reflux ratio R/E=0.7 under steady-state operating conditions.

The crude aniline used contained the key components in the following concentrations:

|            | wt. %    |
|------------|----------|
| benzene      | 0.0550%  |
| aniline      | 99.8299% |
| phenol       | 0.0556%  |
| diphenylamine | 0.0406%  |

After direct addition of NaOH solution to the crude aniline and mixing the two liquids in the pump, the crude aniline had the following concentrations of the key components:

|            | wt. %    |
|------------|----------|
| benzene      | 0.0519%  |
| aniline      | 99.8808% |
| phenol       | 0.0068%  |
| diphenylamine | 0.0425%  |

A smaller concentration of phenol was detected by GC analysis, which is attributed to the conversion of phenol by NaOH into high-boiling (not accessible to GC) Na phenolate.

After separation by distillation of the crude aniline into low-boiling components (head product), high-boiling components (base product) and moderate-boiling components (side-stream), the pure aniline withdrawn as the side-stream had the following concentrations of key components:

|            | wt. %    |
|------------|----------|
| benzene      | 0.0011%  |
| aniline      | 99.9942% |
| phenol       | 0.0006%  |
| diphenylamine | 0.0000%  |

Example 3

50 wt. % NaOH solution was metered into crude aniline in the molar ratio of phenol to NaOH of 1:1. The two liquids were mixed using a gear pump. The column was operated at an absolute pressure of 133 mbar and a reflux ratio R/E=0.8 under steady-state operating conditions.

The crude aniline used contained the key components in the following concentrations:

|            | wt. %    |
|------------|----------|
| benzene      | 0.0550%  |
| aniline      | 99.8299% |
| phenol       | 0.0556%  |
| diphenylamine | 0.0406%  |

After direct addition of NaOH solution to the crude aniline and mixing the two liquids in the pump and subsequent distillation, the crude aniline had the following concentrations of the key components:

|            | wt. %    |
|------------|----------|
| benzene      | 0.0002%  |
| aniline      | 99.9975% |
| phenol       | 0.0009%  |
| diphenylamine | 0.0000%  |

Example 4

32 wt. % NaOH solution was metered into the side-stream reflux in the distillation of crude aniline in a side-stream column, in the molar ratio of phenol (in the crude aniline feed) to NaOH of 1:1.4. The two liquids were mixed by convection. The column was operated at an absolute pressure of 133 mbar and a reflux ratio R/E=0.8 under steady-state operating conditions.

The crude aniline used contained the key components in the following concentrations:

|            | wt. %    |
|------------|----------|
| benzene      | 0.0502%  |
| aniline      | 99.8347% |
| phenol       | 0.0553%  |
| diphenylamine | 0.0410%  |

The side-stream product (pure aniline) obtained under steady-state operation while adding the NaOH solution to the side-stream reflux, mixing the NaOH solution with the side-stream reflux (pure aniline) and distillation contained the key components in the following concentrations:

|            | wt. %    |
|------------|----------|
| benzene      | 0.0007%  |
| aniline      | 99.9921% |
| phenol       | 0.0028%  |
| diphenylamine | 0.0000%  |

Example 5

5 wt. % NaOH solution was metered into crude aniline in the molar ratio of phenol to NaOH of 1:0.95. The two liquids were mixed using a gear pump. The column was operated at an absolute pressure of 133 mbar and a reflux ratio R/E=0.8 under steady-state operating conditions.

The crude aniline used contained the key components in the following concentrations:

|  | wt. % |
| --- | --- |
| benzene | 0.0902% |
| aniline | 99.7041% |
| phenol | 0.0440% |
| diphenylamine | 0.1359% |

After direct addition of NaOH solution to the crude aniline and mixing the two liquids in the pump and subsequent separation by distillation of the crude aniline into low-boiling components (head product), high-boiling components (base product) and moderate-boiling components (side-stream), the pure aniline withdrawn as the side-stream had the following concentrations of key components:

|  | wt. % |
| --- | --- |
| benzene | 0.0015% |
| aniline | 99.9887% |
| phenol | 0.0038% |
| diphenylamine | 0.0000% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of aniline comprising:
   a) hydrogenating nitrobenzene in the presence of a catalyst to produce crude aniline, and
   b) purifying the crude aniline by single- or multi-stage distillation,
in which an aqueous alkali metal hydroxide solution is added to the crude aniline prior to distillation and/or during distillation of the crude aniline, and the aqueous alkali metal hydroxide solution amount is adjusted to maintain a molar ratio of alkali metal hydroxide to phenolic compounds present in the crude aniline between 0.1:1 and 10:1,
   c) partially discharging sump from the distillation,
   d) washing the sump with water or diluted alkali metal hydroxide solution to reduce phenolate salt concentration,
   e) separating the washed sump into an organic phase and an aqueous phase, and
   f) recycling the organic phase to the distillation.

2. The process of claim 1 in which a) is conducted in gas phase under adiabatic conditions in a fixed bed reactor in the presence of a Pd-containing catalyst and any hydrogen not reacted in a) is recycled.

3. The process of claim 1 in which sodium and/or potassium hydroxide solution is used as the alkali metal hydroxide solution.

4. The process of claim 1 in which the alkali metal hydroxide solution contains alkali metal hydroxide in concentrations between 0.1 and 55 wt. %, with respect to the weight of the aqueous alkali metal hydroxide solution.

5. The process of claim 1 in which the alkali metal hydroxide solution is mixed with the crude aniline prior to distillation by static or dynamic mixing elements.

6. The process of claim 1 in which the distillation is performed in one step in a side-stream column and low-boiling components are removed at the column head, high-boiling components are removed as base product and purified aniline is removed as a side-stream.

7. The process of claim 1 in which the distillation is performed in one step in a separating partition column and low-boiling components are removed at the column head, high-boiling components are removed as base product and purified aniline is removed as a side-stream.

8. The process of claim 6 in which vapors withdrawn at the column head are condensed in a two-stage condensation process.

9. The process of claim 7 in which vapors withdrawn at the column head are condensed in a two-stage condensation process.

10. The process of claim 1 in which distillation is first conducted in a low-boiling column where low-boiling components and water are withdrawn at the column's head and a mixture comprising aniline and alkali metal hydroxide is produced at the base, and the base mixture containing aniline and alkali metal hydroxide is separated in a further distillation step.

11. The process of claim 1 in which low-boiling compounds are removed by distillation from the crude aniline before adding the alkali metal hydroxide solution, high-boiling components are separated by distillation from the crude aniline after adding the alkali metal hydroxide solution, purified aniline is obtained at the column head product and high-boiling components are obtained as base product.

12. The process of claim 11 in which the high-boiling components obtained as the base product are concentrated in a distillation column.

* * * * *